(12) United States Patent
Piantoni et al.

(10) Patent No.: US 11,396,137 B2
(45) Date of Patent: Jul. 26, 2022

(54) ROTARY DEVICE FOR WELDING A CONTINUOUS WEB

(71) Applicant: GDM S.P.A., Bologna (IT)

(72) Inventors: Matteo Piantoni, Albino (IT); Gabriele Resmini, Vailate (IT); Maurizio Spatti, Sulzano (IT); Aldo Fusar Poli, Offanengo (IT); Andrea Duchini, Castelleone (IT); Enrico Campagnoli, S. Giovanni in Persiceto (IT); Luca Borderi, Sasso Marconi (IT); Andrea Biondi, Bologna (IT); Gianluca Parisini, Bologna (IT)

(73) Assignee: GDM S.P.A., Bologna (IT)

( * ) Notice: Subject to any disclaimer, the term of this patent is extended or adjusted under 35 U.S.C. 154(b) by 0 days.

(21) Appl. No.: 16/950,219

(22) Filed: Nov. 17, 2020

(65) Prior Publication Data

US 2021/0187870 A1 Jun. 24, 2021

(30) Foreign Application Priority Data

Dec. 19, 2019 (IT) .......................... 102019000024712

(51) Int. Cl.
*B29C 65/00* (2006.01)
*B29C 65/78* (2006.01)
(Continued)

(52) U.S. Cl.
CPC ........ *B29C 65/7885* (2013.01); *B29C 65/086* (2013.01); *B29C 65/7894* (2013.01);
(Continued)

(58) Field of Classification Search
CPC . B29C 65/083; B29C 65/086; B29C 65/7876; B29C 65/7885; B29C 66/433
See application file for complete search history.

(56) References Cited

U.S. PATENT DOCUMENTS 9,259,359 B2 * 2/2016 Fujita ................ A61F 13/15585
2004/0106506 A1 6/2004 Ninomiya et al.
(Continued)

FOREIGN PATENT DOCUMENTS

GB 2280636 A 2/1995
WO 2019212767 A1 11/2019

OTHER PUBLICATIONS

Italian Search Report dated Jun. 5, 2020 from counterpart Italian Patent Application No. 201900024712.

*Primary Examiner* — Philip C Tucker
*Assistant Examiner* — Nickolas R Harm
(74) *Attorney, Agent, or Firm* — Shuttleworth & Ingersoll, PLC; Timothy J. Klima

(57) ABSTRACT

A rotary device for welding a continuous web includes a rotary element, support elements for supporting the web, supported by the rotary element, and a plurality of welding units for welding the web. Each welding unit passes from a non-operating position to an operating position and vice versa, and includes a first movement device for commanding a relative rotation of an anvil element relative to a welding tip and a second movement device for moving the anvil element relative to the welding tip such that a contact surface of the anvil element and a contact surface of the welding tip make contact with a portion of the web in a zone between them, and vice versa. First and second drive mechanisms drive the first and second movement devices. The first and second drive mechanisms are configured to vary a positioning of the welding tip relative to the axis.

14 Claims, 2 Drawing Sheets

(51) Int. Cl.
 *B29C 65/08* (2006.01)
 *B29L 31/48* (2006.01)
 *B29L 31/00* (2006.01)

(52) U.S. Cl.
 CPC ........ *B29C 66/8221* (2013.01); *B29C 65/083* (2013.01); *B29C 65/7876* (2013.01); *B29C 66/433* (2013.01); *B29L 2031/4878* (2013.01); *B29L 2031/7128* (2013.01)

(56) References Cited

U.S. PATENT DOCUMENTS

| | | | |
|---|---|---|---|
| 2012/0157281 A1* | 6/2012 | Schneider | A61F 13/496 |
| | | | 493/379 |
| 2018/0207877 A1* | 7/2018 | Sablone | B29C 66/1122 |
| 2019/0160757 A1* | 5/2019 | Hiroyasu | A61F 13/49 |

* cited by examiner

ROTARY DEVICE FOR WELDING A CONTINUOUS WEB

This application claims priority to Italian Patent Application 102019000024712 filed Dec. 19, 2019, the entirety of which is incorporated by reference herein.

BACKGROUND OF THE INVENTION

This invention relates to a rotary welding device of a continuous web.

In particular, the device according to this invention is configured to weld the web along a direction transverse to the web feed direction according to a predetermined weld spacing.

SUMMARY OF THE INVENTION

As is known, the rotary welding devices use a rotary element supporting a plurality of welding units configured to weld the continuous web during rotation of the rotary element about its own axis of rotation.

The radial positioning of the welding units, relative to the axis of rotation of the rotary element, defines a predetermined working circumference of the welding units, defining a respective weld spacing.

In order to vary the welding step of the device, it is necessary to vary the radial positioning of the welding units relative to the axis of rotation of the rotary element, in such a way as to determine the operating circumference along which the desired welding step is obtained.

In this context, in order to be able to vary the step for welding the continuous web, the need has been felt of making a rotary device for welding a continuous web comprising an element rotating about its own axis of rotation, one or more elements for supporting the continuous web, supported by the rotary element, and a plurality of units for welding the continuous web supported by the rotary element.

Each welding unit is configured to pass from a non-operating position to an operating position and vice versa.

Each welding unit comprises a respective welding tip and a respective anvil element which is movable relative to the welding tip.

Each welding unit comprises respective first movement means configured to drive the anvil element in rotation relative to the welding tip from an initial position, where the anvil element is angularly spaced from the welding tip, to a final position, and vice versa At the final position, the surface (7a) of the welding tip (7) and the surface (8a) of the anvil element (8) are parallel to each other and the axis (7b) at right angles to said surface (7a) of the welding tip and the axis (8b) at right angles to the surface (8a) of the anvil element (8) are aligned along a same axis of alignment (V).

Each welding unit comprises second movement means for moving the anvil element relative to the welding tip from a starting position, where the surface of the welding tip and the surface of the anvil element are parallel and aligned with each other along a same axis of alignment, to an arrival position, where the surface of the anvil element and the surface of the welding tip contact a respective portion of continuous web in a respective zone interposed between them, and vice versa.

First drive means drive the first movement means to cause the anvil element to pass from the initial position to the final position and vice versa.

Second drive means drive the second movement means to cause the passage from the starting position to the arrival position, and vice versa.

The first drive means and the second drive means are configured to vary the relative positioning of the welding tip relative to the axis of rotation of the rotary element.

Advantageously, the first drive means and the second drive means allow the operating circumference of the respective welding units to be determined according to the weld spacing required.

BRIEF DESCRIPTION OF THE DRAWINGS

Further features of the invention and its advantages are more apparent in the following non-limiting description of preferred but non-exclusive embodiments of a rotary welding device for a continuous web, as illustrated in the accompanying drawings, in which.

DESCRIPTION OF THE PREFERRED EMBODIMENTS

The numeral 1 in this specification denotes a rotary welding device of a continuous web.

The device 1 of this specification is configured to weld a continuous web 2 according to a weld spacing P.

The continuous web 2 has at least two superposed edges intended to be welded by the device 1 according to a weld spacing P.

The continuous web 2 has a predominant longitudinal extension L.

The device 1 is configured to weld the continuous web 2 along a direction T transverse to the longitudinal direction of extension L.

Figure 1:
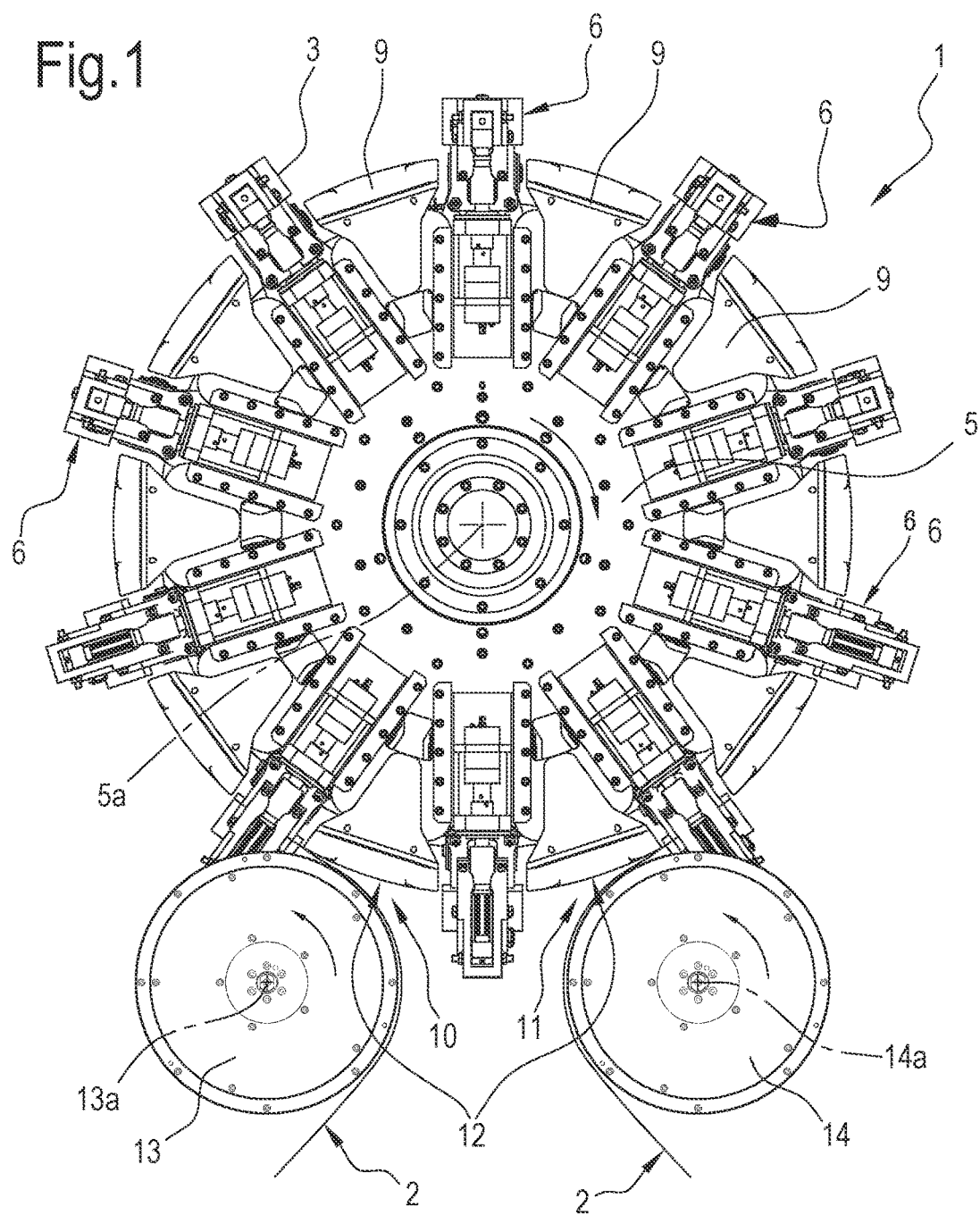
FIG. 1 is a schematic front view of a rotary welding device of absorbent articles according to the invention.
Figure 2:
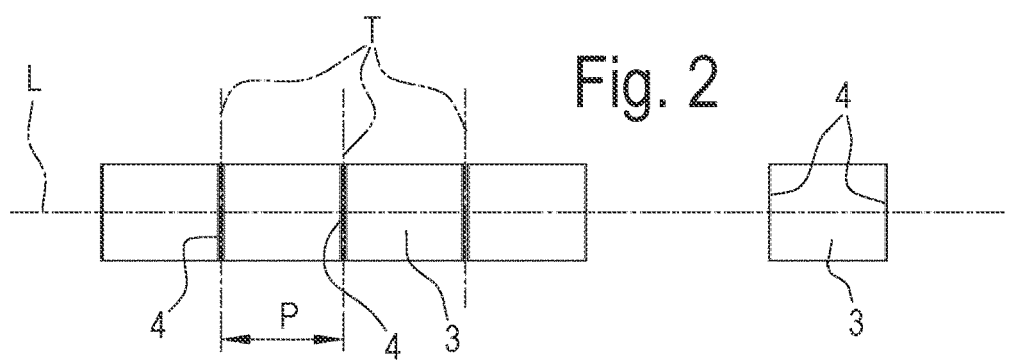
FIG. 2 is a schematic plan view of a continuous web processed by the device of FIG. 1.

More specifically, with reference to FIG. 2, the device 1 makes a plurality of welds along the transverse direction T of the continuous web 2 in respective welded zones 4 according to a weld spacing P.

For example, the continuous web 2 is a continuous strip of absorbent articles, in particular a continuous web of pants nappies, so-called "training pants".

The continuous strip is a succession of absorbent articles folded along the center line of the absorbent pad.

For example, the device according to invention is configured to weld a continuous web of absorbent articles, or nappies, to weld the elasticized side gathers of nappy pants around the waist of the user.

According to a further example, the continuous web 2 is a continuous strip of pouches containing liquids, specifically liquid food products such as beverages, for example, or solid food products such as infusion substances.

Downstream of the device 1, cutting means, not illustrated, act at each welded zone 4 of the continuous web 2, in particular at the center line of each, for separating individual lengths 3 of continuous web 2.

The rotary welding device 1 comprises a rotary part 5 which rotates about its axis of rotation 5a.

The axis of rotation 5a of the rotary part 5 is preferably a horizontal axis.

Alternatively, the axis of rotation 5a of the rotary part 5 is a vertical axis.

The device 1 comprises a plurality of welding units 6 for welding the continuous web 2.

The welding units 6 are mounted on the rotary part 5 and thus rotate about the axis of rotation 5a of the rotary part 5.

The welding units 6 are equispaced from each other angularly about the axis of rotation 5a of the rotary part 5.

The circumferential spacing of the welding units 6 determines the weld spacing "P" of the welded zones 4 of the continuous web 2.

The diameter defined by the spacing of the welding units 6 about the axis of rotation 5a of the rotary part 5 is therefore a changeover parameter.

Each welding unit 6 comprises a respective welding tip 7 and a respective opposing element 8, or anvil element 8, of the welding tip 7.

The anvil element 8 of each welding unit 6 has a contact surface 8a for a respective portion of the continuous web 2.

The contact surface 8a of the anvil element 8 has an axis 8b which is orthogonal to the surface 8a.

The contact surface 8a has a predetermined welding pattern.

The welding tip 7 of each welding unit 6 has a contact surface 7a for a respective portion of the continuous strip 2.

The contact surface 7a of the welding tip 7 has an axis 7b which is orthogonal to the surface 7a.

Preferably, the welding tip is an ultrasound welding tip 7.

Alternatively, the welding tip 7 is a thermomechanical tip.

Preferably, each welding tip 7 of a welding unit 6 is disposed towards the inside of the rotary part 5 and the respective anvil element 8 towards the outside.

In this way, the relative overall dimensions are optimized, making this solution more compact and, therefore, preferable.

Each welding unit is configured to pass from a non-operating position to an operating position and vice versa.

Figure 3:
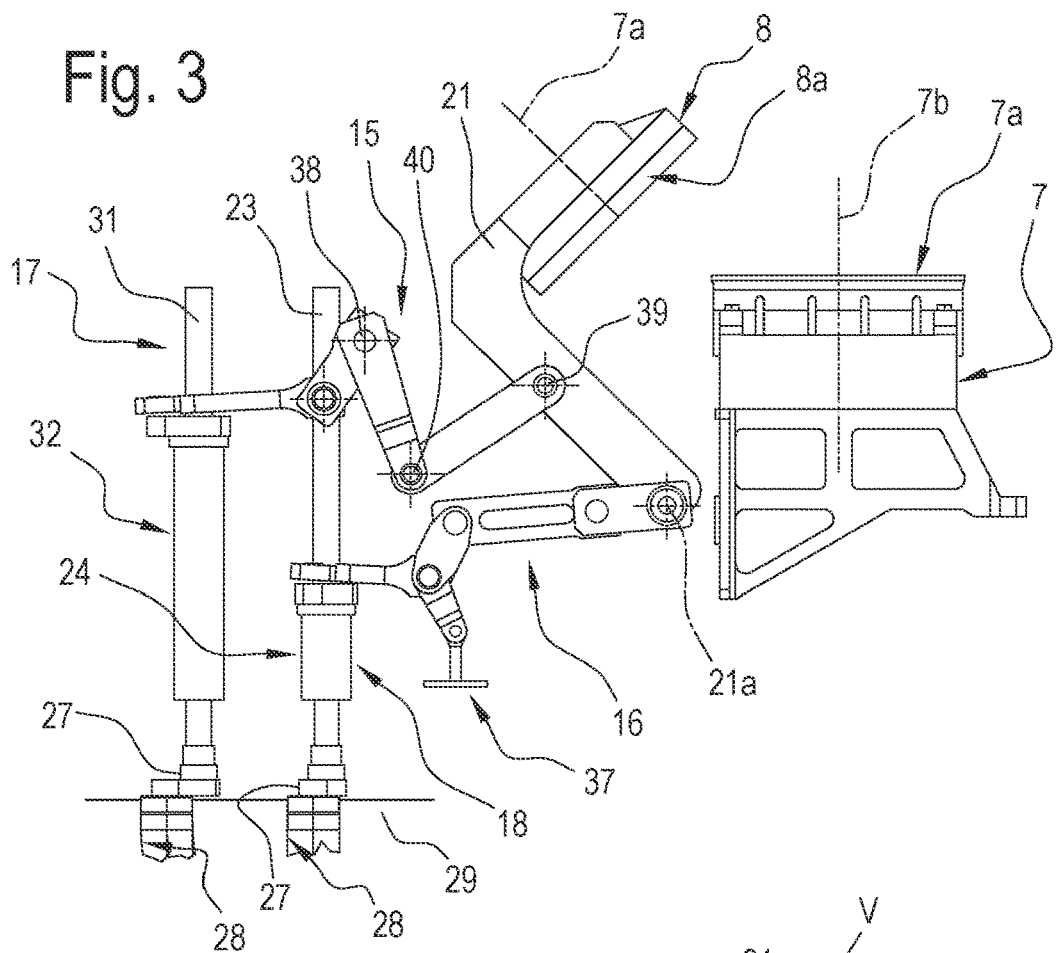
FIG. 3 is a schematic side view of the welding unit of FIG. 1 in a non-operating position.
Figure 4:
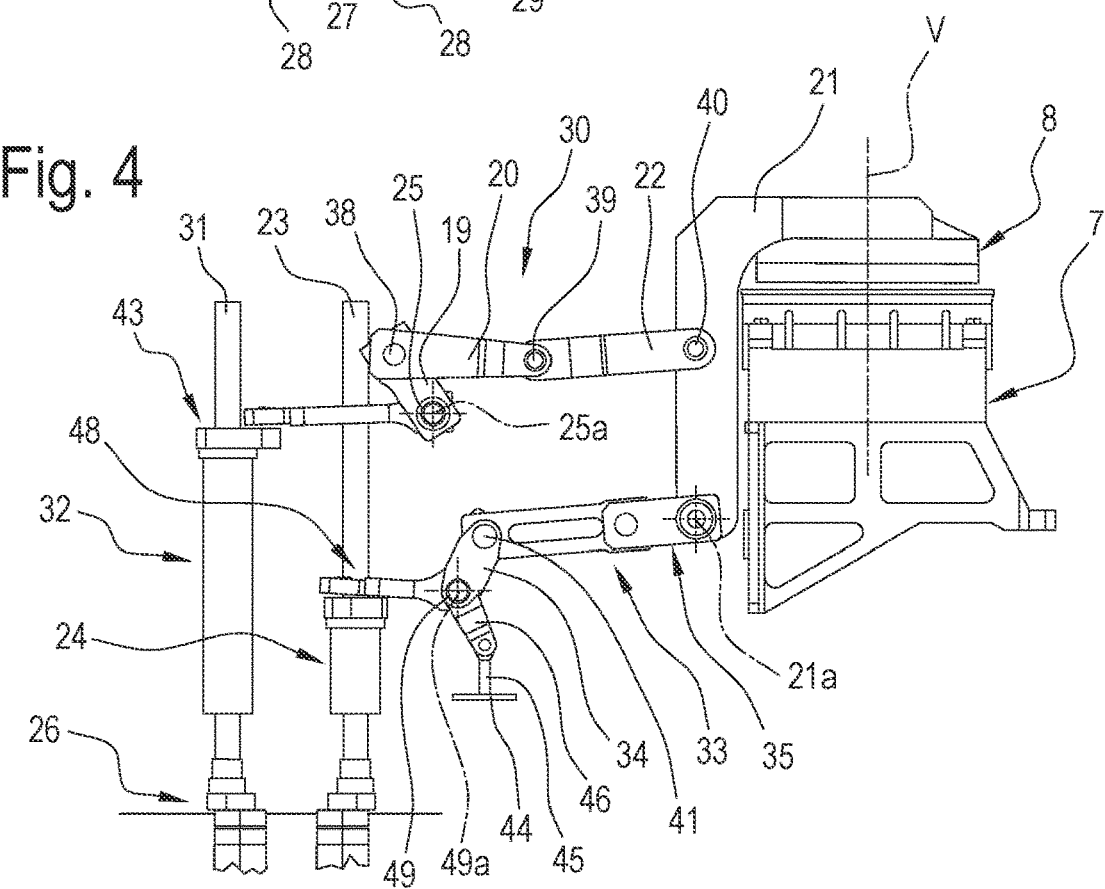
FIG. 4 is a schematic side view of the welding unit of FIG. 1 in an operating position.

At the non-operating position, the surface 8a of the anvil element 8 is relatively spaced from the surface 7a of the welding tip 7, which contacts the portion of continuous web 2 (see FIG. 3).

At the non-operating position, the axis 7b which is orthogonal to the surface 7a of the welding tip is incident upon the axis 8b which is orthogonal to the surface 8a of the anvil element 8.

At the operating position of the welding unit 6, the surface 8a of the anvil element 8 and the surface 7a of the welding tip 7 contact a respective portion of continuous web 2 interposed between them and intended to become a welded zone 4.

At the operating position, the axis 7b which is orthogonal to the surface 7a of the welding tip and the axis 8b which is orthogonal to the surface 8a of the anvil element 8 are aligned along the same alignment axis V.

The device 1 comprises a plurality of supporting elements 9 for supporting the continuous web 2.

The supporting elements 9 for supporting the continuous strip 2 are mounted on the rotary part 5 and thus rotate about the axis of rotation 5a of the rotary part 5 (see FIG. 3).

The welding units 6 and the supporting elements 9 are mounted alternately with each other.

In other words, each welding unit 6 is interposed between a respective pair of supporting elements 9.

Each supporting element 9 has a retaining surface 12 for holding the continuous web 2.

The retaining surface 12 of each supporting element 9 is preferably a curved surface.

Alternatively, the retaining surface 12 of each supporting element 9 is preferably a flat surface.

Preferably, the supporting elements 9 are configured to hold the continuous web 2 by suction.

In this regard, the retaining surface 12 is provided with a pattern of suction holes.

The device 1 comprises a station 10 for feeding the continuous web 2 to be welded and an outfeed station 11 of the welded continuous web 2.

The continuous web 2 is fed through the feed station 10 by a roller 13, preferably a suction roller, which rotates about its axis of rotation 13a in such a way that wraps around, without slipping, the retaining surfaces 12 of the supporting elements 9.

It should be noted that, if the continuous web 2 is a continuous strip of absorbent articles, it is wrapped around the supporting elements 9 of the device 1 in such a way that the continuous succession of superposed elasticized gathers faces towards the front of the device accessible to the operator.

The welded continuous web 2 is fed out through the outfeed station 11 by a roller 14, preferably a suction roller, which rotates about its axis of rotation 14a.

The axis of rotation 13a of the feed roller 13 of the continuous web 2 and the axis of rotation 14a of the conveying roller 14 of the welded continuous web 2 are parallel.

The axis of rotation 5a of the rotary element 5 is parallel to the axes of rotation 13a, 14a of the feed roller 13 of the continuous web 2 and of the conveying roller 14 of the welded continuous web 2.

According to this invention, each welding unit 6 comprises first movement means 15 for moving the anvil element 8 relative to the welding tip 7 by imparting a movement whereby the anvil element 8 moves towards the welding tip 7 and a movement whereby the anvil element 8 moves away from the welding tip 7.

The movement towards consists in positioning the anvil element 8 at a position where it is aligned with the welding tip 7—that is to say, a mutual position such that the contact surface 8a of the anvil element 8 is parallel to the contact surface 7a of the welding tip 7 and such that the axis 8b which is orthogonal to the contact surface 8a of the anvil element 8 is aligned with the axis 7b which is orthogonal to the contact surface 7a of the welding tip 7 along the same alignment axis V.

The first movement means 15 are configured to drive the anvil element 8 in rotation relative to the welding tip 7 from an initial position, where the anvil element 8 is angularly spaced from the welding tip 7, to a final position, where the surface 7a of the welding tip 7 and the surface 8a of the anvil element 8 are parallel and aligned with each other along the same alignment axis V, and vice versa.

At the initial position, the direction of the axis 8b which is orthogonal to the surface 8a of the anvil element 8 is incident upon the direction of the axis 7b which is orthogonal to the surface 7a of the welding tip 7, in particular in such a way as to make an acute angle.

The first movement means 15 comprise at least one articulated system 30 comprising at least one control crank 19, and a lever 21, moved by the crank 19, which oscillates relative to its axis 21a of oscillation.

The oscillation of the lever 21 about the axis of oscillation 21a causes the anvil element 8 to move towards and away from the welding tip 7—that is to say, causes the anvil element 8 to pass from the initial position to the final position, and vice versa, relative to the welding tip 7.

The first movement means 15 comprise at least a first connecting rod 20, connected to the crank 19, and a second connecting rod 22 connected to the first connecting rod 20 and to the lever 21.

The first connecting rod (20) and the second connecting rod (22) transmit the controlled movement from the crank (19) to the lever (21).

In particular, the second connecting rod 22 is connected to the lever 21 at a central position relative to the main longitudinal extension of the lever 21.

The first connecting rod 20 is rotatably connected to the crank 19 by a pin 38.

The pin 38 connecting the first connecting rod 20 to the crank 19 is integral with the crank 19.

The second connecting rod 22 is connected in a rotatable fashion to a respective portion of the lever 21 by a pin 39 which is integral with the lever 21.

The first connecting rod 20 is rotatably connected to the second connecting rod 22 by a pin 40.

The crank 19, the first connecting rod 20, the second connecting rod 22 and the lever 21 of the first movement means 15 define an articulated "toggle" system.

The first movement means 15 comprise a pair of articulated systems 30, located opposite one another.

According to an alternative embodiment, with reference to each welding unit 6, the first movement means 15 comprise a double articulated "toggle" system, driven synchronously.

The anticlockwise rotation of the crank 19 causes the relative movement of the first connecting rod 20 and of the second connecting rod 22, which oscillates the respective lever 21 about the axis of oscillation 21a, in a clockwise direction, so that the anvil element 8 passes from the initial position to the final position, and vice versa, relative to the welding tip 7.

A clockwise counter-rotation of the crank 19, with reference to the embodiment illustrated, causes the anticlockwise oscillation of the respective lever 21 about the axis of oscillation 21a, so that the anvil element 8 moves away from the welding tip 7, that is to say, passes from the final position to the initial position.

At the final position of the anvil element 8 relative to the welding tip 7, at least the first connecting rod 20 and the second connecting rod 22 are aligned with each other at a position inclined to the position of the lever 21.

In particular, in the position of reciprocal alignment, at least the first connecting rod 20 and the second connecting rod 22 are positioned along a direction at right angles to the position of the lever 21.

In this position of reciprocal alignment, the connecting pins 38, 39, 40 from the crank 19 to the lever 21 are positioned parallel to each other.

First drive means 17 control the movement of the first movement means 15.

The configuration adopted by the crank 19, the first connecting rod 20, the second connecting rod 22 and lever 21 at the final position of the anvil element 8 relative to the welding tip 7, is such that the welding forces are not transferred to the first drive means 17, since the forces are de-multiplied by the configuration adopted by the articulated system 30 of the first movement means 15.

The first drive means 17 control the movement of the crank 19 of the articulated system 30 of the first movement means 15.

The first drive means 17 are configured to be movable in a radial direction, relative to the axis of rotation 5a of the rotary element 5.

Advantageously, the radial movement of the first drive means 17 allows the working circumference of each welding unit 6 to be varied without modifying the elements of the articulated system 30 of the first movement means 15 which thus maintains its motion transmission ratios.

Each welding unit 6 comprises second movement means 16 for moving the anvil element 8 relative to the welding tip 7 from a starting position, where the contact surface 8a of the of the anvil element 8 and the contact surface 7a of the welding tip 7 are parallel and aligned with each other along the same alignment axis V, to an arrival position, where the contact surface 8a of the anvil element 8 and the contact surface 7a of the welding tip 7 contact the continuous web 2 interposed between them.

The arrival position corresponds to the operating position of the welding unit 6.

From the starting position to the arrival position, the anvil element 8 translates towards the respective welding tip 7 until it comes into contact with the continuous web 2 that is interposed between them.

Conversely, the second movement means 16 are configured to translate the anvil element 8 away from the welding tip 7, thus disengaging the continuous web 2 interposed between them.

The second movement means 16 are driven by second drive means 18.

The second movement means 16 comprise at least one articulated system 33 comprising a crank 34 for controlling a connecting rod 35 rotatably connected to the axis 21a of oscillation of the lever 21.

The crank 34 and the connecting rod 35 are rotatably connected by a pin 41.

The pin 41 is connected to the crank 34.

The crank 34, the connecting rod 35 and the lever 21 define an articulated "toggle" system 33.

According to an alternative embodiment, with reference to each welding unit 6, the second movement means 16 comprise a double articulated "toggle" system, driven synchronously.

At the arrival position, the connecting rod 35 is positioned along a direction at right angles to the crank 34.

At the arrival position, the connecting rod 35 is positioned along a direction at right angles to the lever 21.

The second movement means 16 comprise a pair of articulated systems 33, located opposite each other.

The second movement means 16 comprise a pneumatic system 37 configured for determining a translation towards or away from the anvil element 8 relative to the welding tip 7, and vice versa, by means of the above-mentioned articulated system 33.

The pneumatic system 37 allows applying and maintaining a predetermined pressure between the anvil element 8 and the welding tip 7 so that the pressure remains as constant as possible during the entire welding process—that is, for as long as the welding unit 6 is at the operating position.

The zone of the continuous web 2 which is interposed between the surface 8a of the anvil element 8 and the surface 7a of the welding tip 7 is welded when the welding tip 7 is actuated to make the welded zone 4.

The pneumatic system 37 is connected to the crank 34 of the second movement means 16.

The pneumatic system 37 comprises a piston 44 whose rod 45 is rotatably connected to an arm 46 rotatably connected to the crank 34 of the second movement means 16.

At the arrival position, the arm 46 to which the rod 45 of the piston 44 is connected is aligned with the arm 46, connected to the crank 34, and to the crank 34.

This alignment advantageously makes it possible to transmit the force generated by the pneumatic system 37 directly to the welding tip 7.

The lever ratio of the articulated system 33 allows doubling of the force generated by the pneumatic system 37.

Advantageously, this alignment allows the forces generated by the pneumatic system to be isolated from the articulated system 33 of the second movement means 16, preventing them from affecting the second drive means 18.

The second drive means 18 control the movement of the crank 19 of the articulated system 30 of the first movement means 15.

The second drive means 18 are configured to be movable in a radial direction, relative to the axis of rotation 5a of the rotary element 5.

Advantageously, the radial movement of the second drive means 18 allows the working circumference of each welding unit 6 to be varied without modifying the elements of the articulated system 33 of the second movement means 16 which thus maintains its motion transmission ratios.

The first drive means 17 and the second drive means 18 comprise a single control member 26 and a respective first drive transmission unit 32 and a second drive transmission unit 24.

The control unit 26 comprises a drum 29, rotating about a respective axis of rotation, having on its peripheral surface several sliding tracks 28 for cam follower rollers 27.

The first motion transmission unit 32 comprises a rod-shaped element 31, which has at one end at least one cam follower roller 27 configured to engage in a respective track 28 of the drum 29.

The rod-shaped element 31 extends in a direction radial to the axis of rotation 5a of the rotary element 5.

The track 28 of the drum is configured, along at least one stretch, to impart a rotation of the rod-shaped element 31.

The rotation of the rod-shaped element 31 causes the movement of the first movement means 15.

The first drive transmission unit 32 comprises at least one rotation transmission element 43 imparted to the rod-shaped element 31 to the crank 19 of the articulated system 30 of the first movement means 15.

The transmission element 43 is slidably constrained to the rod-shaped element 31 for varying the radial position of the anvil element 8.

The transmission element 43, whatever position adopted along the rod-shaped element 31, is constrained to the rotation of the rod-shaped element 31.

The crank 19 is rotatably connected to the transmission element 43 by a shaft 25, which rotates about its axis of rotation 25a.

The cranks 19 of the double articulated system 30 are connected to the shaft 25.

The second motion transmission unit 24 comprises a rod-shaped element 23, which has at one end at least one cam follower roller 27 configured to engage in a respective track 28 of the drum 29.

The rod-shaped element 23 extends in a direction radial to the axis of rotation 5a of the rotary element 5.

The track 28 of the drum is configured, along at least one stretch, to impart a rotation of the rod-shaped element 23.

The rotation of the rod-shaped element 23 causes the actuation of the motion transmission unit 32 for moving the second movement means 16.

The second drive transmission unit 24 comprises at least one rotation transmission element 48 imparted to the rod-shaped element 23 to the crank 19 of the articulated system 33 of the second movement means 16.

The transmission element 48 is slidably constrained to the rod-shaped element 23 for being able to vary the radial position of the anvil element 8.

The transmission element 48, whatever position adopted along the rod-shaped element 23, is constrained to the rotation of the rod-shaped element 23.

The crank 34 is rotatably connected to the transmission element 48 by a shaft 49, which rotates about its axis of rotation 49a.

The cranks 34 of the double articulated system 33 are connected to the shaft 49.

The rotation of the rod-shaped element 23 causes the actuation of the motion transmission unit 24 for moving the second movement means 16.

Advantageously, the possibility of translating the motion transmission element 43, 48 of the first drive means 17 and the second drive means 18 along the respective rod-shaped element 31, 23 makes it possible to vary the position of the anvil element 8 relative to the axis of rotation 5a of the rotary element 5.

This position variation makes it possible to define an operating circumference as a function of the welding spacing.

What is claimed is:

1. A rotary device for sealing a continuous web, comprising:
   a rotary carousel rotatable about an axis of rotation thereof, a supporting element including a retaining surface, for supporting a continuous web supported by the rotary carousel and a plurality of welding units for welding the continuous web supported by the rotary carousel;
   each welding unit being configured to pass from a non-operating position to an operating position and vice versa;
   each welding unit comprising a respective welding tip and a respective anvil connected to a movable lever such that the anvil is movable relative to the welding tip;
   each welding unit comprising a respective first movement mechanism including a first articulated mechanism connected to the lever and configured to drive the anvil in rotation relative to the welding tip from an initial position, where the anvil is angularly spaced from the welding tip, to a final position, and vice versa;
   at the final position, a surface of the welding tip and a surface of the anvil being parallel to each other and the axis at right angles to the surface of the welding tip and the axis at right angles to the surface of the anvil are aligned along a same axis of alignment;
   each welding unit comprising a second movement mechanism including a second articulated mechanism connected to the lever and configured for moving the anvil relative to the welding tip from a starting position, where the surface of the welding tip and the surface of the anvil are parallel and aligned with each other along the same axis of alignment, to an arrival position, where a contact surface of the anvil and a contact surface of the welding tip contact a respective portion of the continuous web in a respective zone interposed between them, and vice versa;
   a first drive mechanism configured to drive the first movement mechanism to cause the anvil to pass from the initial position to the final position and vice versa;
   a second drive mechanism configured to drive the second movement mechanism to cause passage from the starting position to the arrival position, and vice versa;

the first drive mechanism and the second drive mechanism being configured to vary a relative positioning of the welding tip relative to the axis of rotation of the rotary carousel.

2. The device according to independent claim 1, wherein for each welding unit the first drive mechanism comprises a first rod-shaped member and a first motion transmission member configured for transmitting motion to the first movement mechanism; the first motion transmission member being shaped to slidably engage the first rod-shaped member to translate along the first rod-shaped member and vary a relative position of the first motion transmission member along the first rod-shaped member.

3. The device according to claim 2, wherein for each welding unit the first rod-shaped member of the first drive mechanism is configured to be rotated; the rotation of the first rod-shaped member causing actuation of the first movement mechanism via the first motion transmission member.

4. The device according to claim 3, wherein for each welding unit the second drive mechanism comprises a second rod-shaped member and a second motion transmission member configured for transmitting motion to the second movement mechanism; the second motion transmission member being slidably constrained to the second rod-shaped member to translate along the second rod-shaped member and vary ails relative position of the second motion transmission member along the second rod-shaped member.

5. The device according to claim 4, wherein for each welding unit the second rod-shaped member of the second drive mechanism is configured to be rotated; the rotation of the second rod-shaped member causing actuation of the second movement mechanism via the second motion transmission member.

6. The device according to claim 5, and further comprising a cam configured to drive the rotation of the first and second rod-shaped members.

7. The device according to claim 1, wherein for each welding unit the first articulated mechanism comprises a crank, moved by the first drive mechanism, with the lever moved by the crank in such a way as to oscillate with respect to a relative axis of oscillation for controlling angular movement of the anvil relative to the welding tip from the initial position to the final position, and vice versa.

8. The device according to claim 7, wherein for each welding unit the first articulated mechanism further includes a first connecting rod, connected to the crank, and a second connecting rod connected to the first connecting rod and to the lever; the first connecting rod and the second connecting rod configured to transmit the movement from the crank to the lever.

9. The device according to claim 8, wherein for each welding unit the second articulated mechanism comprises a crank, moved by the second drive mechanism, and a connecting rod rotatably connected to an axis of oscillation of the lever.

10. The device according to claim 9, wherein for each welding unit the second movement mechanism comprises a pneumatic system configured for determining a translation of the anvil towards or away from the welding tip, by the second articulated mechanism.

11. The device according to claim 1, wherein for each welding unit the the second articulated mechanism comprises a crank, moved by the second drive mechanism, and a connecting rod rotatably connected to an axis of oscillation of the lever.

12. The device according to claim 11, wherein for each welding unit the second movement mechanism comprises a pneumatic system configured for determining a translation of the anvil towards or away from the welding tip, by the second articulated mechanism.

13. The device according to claim 1, wherein for each welding unit the second drive mechanism comprises a second rod-shaped member and a second motion transmission member configured for transmitting motion to the second movement mechanism; the second motion transmission member being slidably constrained to the second rod-shaped member to translate along the second rod-shaped member and vary a relative position of the second motion transmission member along the second rod-shaped member.

14. The device according to claim 13 wherein for each welding unit the second rod-shaped member of the second drive mechanism is configured to be rotated; the rotation of the second rod-shaped member causing actuation of the second movement mechanism via the second motion transmission member.

* * * * *